United States Patent [19]

Stelzer et al.

[11] Patent Number: 5,268,479
[45] Date of Patent: Dec. 7, 1993

[54] PROCESS FOR THE PREPARATION OF TERTIARY PHOSPHINES

[75] Inventors: Othmar Stelzer; Klaus-Peter Langhans, both of Wuppertal; Norbert Weferling, Hürth, all of Fed. Rep. of Germany

[73] Assignee: Hoechst Aktiengesellschaft, Frankfurt am Main, Fed. Rep. of Germany

[21] Appl. No.: 984,369

[22] Filed: Dec. 2, 1992

[30] Foreign Application Priority Data

Dec. 14, 1991 [DE] Fed. Rep. of Germany ....... 4141299

[51] Int. Cl.$^5$ .......................... C07F 9/58; C07C 9/50
[52] U.S. Cl. ........................................ 546/21; 556/13; 556/18; 556/21
[58] Field of Search ...................... 546/21; 556/13, 18, 556/21

[56] References Cited

FOREIGN PATENT DOCUMENTS 0386833 9/1990 European Pat. Off. .
1016294 5/1983 U.S.S.R. .
1494130 12/1977 United Kingdom .

Primary Examiner—C. Warren Ivy
Assistant Examiner—Zinna N. Davis
Attorney, Agent, or Firm—Connolly & Hutz

[57] ABSTRACT

A process is specified for the preparation of tertiary phosphines of the formula $$R'PR_2 \text{ or } R_2P\text{—}[CH_2]_3\text{—}PR_2$$

in which R is an aryl, pyridyl or arylsulfonic acid group and R' is an aryl, pyridyl, arylsulfonic acid or n-butyl group, which comprises reacting phosphines of the formula $$H_nPR''_{3-n} \text{ or } H_2P\text{—}[CH_2]_3\text{—}PH_2$$

in which R" is hydrogen or an n-butyl, aryl or pyridyl group and n is 1 or 2 with a halogen compound of the formula $$X\text{-R},$$

in which R has the abovementioned meaning and X is fluorine, chlorine or bromine, in the presence of powdered potassium hydroxide and dimethyl sulfoxide and-/or dimethoxyethane at temperatures between 0 and 100° C., at least 1 mol of potassium hydroxide being used per mole of halogen compound.

6 Claims, No Drawings

PROCESS FOR THE PREPARATION OF TERTIARY PHOSPHINES

The present invention relates to a process for the preparation of tertiary phosphines of the formula $$R'PR_2 \text{ or } R_2P\text{—}[CH_2]_3\text{—}PR_2$$

in which R is an aryl, pyridyl or arylsulfonic acid group and R' is an aryl, pyridyl, arylsulfonic acid or n-butyl group. Also included among the phosphines according to the invention are those compounds in which different aryl or pyridyl radicals are linked to the phosphorus atom.

The phosphines according to the invention are gaining increasing industrial significance as structural units for the preparation of catalysts, as is described in EP-A-0 386 833.

Hitherto the phosphines according to the invention have been prepared by the route of reacting organometallic compounds with organic phosphorus-halogen compounds (EP-A-0 386 833). The expensive starting materials which are used are a disadvantage of this process.

Surprisingly, it has now been found that tertiary phosphines of the formulae specified at the beginning are obtained when phosphines of the formula $$H_nPR''_{3-n} \text{ or } H_2P\text{—}[CH_2]_3\text{—}PH_2$$

in which R'' is hydrogen or an n-butyl, aryl or pyridyl group and n is 1 or 2, are reacted with a halogen compound of the formula $$X\text{-}R$$

in which R is an aryl, pyridyl or arylsulfonic acid group and X is fluorine, chlorine or bromine, in the presence of powdered potassium hydroxide and dimethyl sulfoxide (DMSO) and/or dimethoxyethane (DME) at temperatures between 0 and 100° C., at least 1 mol of potassium hydroxide being used per mole of halogen compound.

Advantageous embodiments of this process are for example when a) powdered potassium hydroxide is suspended in dimethyl sulfoxide and/or dimethoxyethane, the phosphine is added and the halogen compound is metered into this suspension over the course of 0.1 to 2 hours, and this reaction mixture is allowed to react for a further 4 to 12 hours at temperatures between 20 and 100° C.;

b) to purify the tertiary phosphine, the further-reacted reaction mixture is stirred with water and the tertiary phosphine is extracted from it with methylene chloride, the extract is dried over solid potassium hydroxide, the extract is evaporated under a vacuum of 0.01 mbar and at a temperature of 20 to 100° C. and the oily residue is crystallized in ethanol.

The following general method may be applied for the reaction. When reacting PH3, it is recommended that a PH3 slight excess pressure of about 0.1 bar be applied.

Powdered potassium hydroxide is suspended in dimethyl sulfoxide (DMSO) and/or dimethoxyethane (DME) in a stirring apparatus (3-necked flask with stirrer, dropping funnel, reflux condenser and gas inlet tube). Air is removed from the apparatus by introducing nitrogen and the phosphine is then introduced. When reacting PH3, the PH3 is introduced into the suspension as a gas via the gas inlet tube and the apparatus is set under an excess pressure of 0.1 bar and kept at constant pressure by subsequently adding PH3. The halogen compound is then metered in over the course of 0.1 to 2 hours. The reaction mixture may be kept at constant temperature by cooling or heating. After all the halogen compound has been added, the reaction mixture is stirred for a further 4 to 12 hours.

To purify the reaction mixture, the latter is treated with degassed water, with cooling, and extracted with methylene chloride. The organic phase is then dried over solid potassium hydroxide and decanted off. The dried organic phase is evaporated in vacuo and purified by fractional distillation or by crystallization in ethanol.

Examples of reaction products and reaction conditions are listed in the following table.

85% strength potassium hydroxide was used, i.e. it contained about 15% by weight of water as well as the KOH.

The following comments relate to the table:

1) The reaction mixture was stirred with 300 ml of degassed water. The precipitate which separated out was filtered off and washed with 300 ml of water.

2) Two phases formed after the addition of 40 ml of water to the reaction mixture. The upper (organic) phase was separated off, evaporated under vacuum (40° C.; 0.01 mbar) and recrystallized in 50 ml of ethanol.

3) The reaction mixture was treated with 50 ml of water and 250 ml of ethanol. The precipitate which separated out was filtered off, washed with 20 ml of ethanol and recrystallized in 15 ml of water.

4) The DME was distilled off under vacuum (40° C.; 0.01 mbar). The residue was taken up in 20 ml of water and evaporated to 10 ml. The oil which separated out was separated from the aqueous phase and recrystallized from ethanol.

5) The reaction mixture was stirred with 300 ml of water and extracted with 100ml of methylene chloride. A viscous oil remained after evaporation in vacuo (20° C.; 0.1 mbar).

TABLE

| | Starting materials | | | | Reaction conditions | | | | | |
|---|---|---|---|---|---|---|---|---|---|---|
| | Phosphine | Halogen compound | | DMSO/DME | KOH (g) | CH₂Cl₂ | Temp. | Time Reaction | Further reaction | Final product Yield | |
| No. | (g) (mol) | (g) | (mol) | (ml) | (mol) | (ml) | (°C.) | (η) | (η) | (g) (%) |
| 1 | PH₃ | fluorobenzene 9.6 | 0.1 | DMSO 100 | 26.4 0.4 | 100 | 20 100 | 0.5 | 4 | triphenylphosphine 5.3 | 61 |
| 2 | PH₃ | 2-chloropyridine 22.7 | 0.2 | DMSO 800 | 52.8 0.8 | 300 | 20 20 | 1 | 12 | tris(2-pyridyl) phosphine 2.9 | 17 |
| 3 | PH₃ | 2-chloropyridine | | DMSO | 52.8 | 200 | 20 | 2 | | tris(2-pyridyl) | |

TABLE -continued

| No. | Starting materials Phosphine (g) (mol) | Halogen compound (g) (mol) | DMSO/ DME (ml) | KOH (g) (mol) | CH₂Cl₂ (ml) | Reaction conditions Temp. (°C.) | Time Reaction (η) | Further reaction (η) | Final product Yield (g) (%) |
|---|---|---|---|---|---|---|---|---|---|
| | | 56.7   0.5 | 200 | 0.8 | | 20 | | 12 | phosphine 38.5   87 |
| 4 | PH₃ | 3-chloropyridine 22.8   0.2 | DMSO 100 | 26.4 0.4 | | 20 20 | 1 | 12 | tris(3-pyridyl) phosphine 11.4   64 |
| 5 | (2-pyridyl)-phosphine 5.6   0.05 | 3-chloropyridine 11.4   0.1 | DMSO 100 | 13.2 0.2 | 100 | 20 40 | 1 | 4 | (2-pyridyl)bis(3-pyridyl)phosphine 6.0   45 |
| 6 | (2-pyridyl)phosphine 5.6   0.05 | 4-chloropyridine hydrochloride 15.0   0.1 | DMSO 100 | 19.8 0.3 | 100 | 20 40 | 1 | 4 | bis(4-pyridyl)(2-pyridyl)phosphine 6.8   51 |
| 7 | n-butylphosphine 4.5   0.05 | 2-chloropyridine 11.4   0.1 | DMSO 100 | 13.2 0.2 | 100 | 20 20 | 0.25 | 12 | bis(2-pyridyl)-n-butyl-phosphine 6.4   52 |
| 8 | phenylphosphine 110   1.0 | 2-chloropyridine 227   2.0 | DMSO 1000 | 264 4.0 |  | 20 20 | 1 | 12 | bis(2-pyridyl) phenylphosphine 247   94 |
| 9 | PH₃ | 2-chloropyridine 11.4   0.1 | DME 100 | 19.8 0.3 |  | 40 40 | 2 | 12 | tris(2-pyridyl) phosphine 7.2   82 |
| 10 | PH₃ | p-fluorobenzenesulfonic acid (K salt) 21.4   0.1 | DMSO 100 | 19.8 0.3 |  | 40 40 | 1 | 12 | tris(4-benzenesulfonic acid) phosphine (K salt) 14.0   68 |
| 11 | bis(3-pyridyl)phosphine 2.3   0.01 | p-fluorobenzenesulfonic acid (K salt) 2.6   0.01 | DME 20 | 1.65 0.025 |  | 20 boiling | 0.3 | 1 | bis(3-pyridyl)(4-benzenesulfonic acid)phosphine (K salt) 2.6   56 |
| 12 | 1,3-diphosphinopropine 5.4   0.05 | 2-chloropyridine 22.7   0.2 | DMSO 100 | 39.6 0.6 | 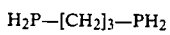 | 5 20 | 0.25 | 12 | 1,3-bis[di(2-pyridyl)phos-phino]propane 13.6   65 |
| 13 | 1,3-diphosphinopropine 5.4   0.05 | 3-chloropyridine 22.7   0.2 | DMSO 100 | 39.6 0.6 |  | 5 20 | 0.25 | 12 | 1,3-bis[di(3-pyridyl)phos-phino]propane 14.9   71 |

We claim:

1. A process for the preparation of tertiary phosphines of the formula

R'PR₂ in which R is an aryl, pyridyl or arylsulfonic acid group and R' is an aryl, pyridyl, arylsulfonic acid or n-butyl group, which comprises reacting phosphines of the formula H$_n$PR''$_{3-n}$ in which R'' is hydrogen or an n-butyl, aryl, or pyridyl group and n is 1 or 2 with a halogen compound of the formula

X-R in which R has the abovementioned meaning and X is selected from the group comprising fluorine, chlorine and bromine, in the presence of powdered potassium hydroxide and at least one aprotic solvent selected from the group comprising dimethyl sulfoxide and dimethoxyethane at temperatures between 0 and 100° C, at least 1 mol of potassium hydroxide being used per mole of halogen compound.

2. The process as claimed in patent claim 1, wherein powdered potassium hydroxide is suspended in the aprotic solvent, the phosphine is added and the halogen compound is metered into this suspension in the course of 0.1 to 2 hours, and this reaction mixture is allowed to react for a further 4 to 12 hours at temperatures between 20 and 100C.

3. The process as claimed in patent claim 1, wherein, to purify the tertiary phosphine, the reacted reaction mixture is stirred with water and the tertiary phosphine is extracted from it with methylene chloride, the extract is dried over solid potassium hydroxide, the extract is evaporated under a vacuum of 0.01 mbar and at a temperature of 20 to 100C. and the oily residue is crystallized in ethanol.

4. A process for the preparation of tertiary phosphines of the formula

R₂P—[CH₂]₃—PR₂ in which R represents an aryl, pyridyl or arylsulfonic acid group, which comprises reacting phosphines of the formula

H₂P—[CH₂]₃—PH₂ with a halogen compound of the formula

X-R in which R has the abovementioned meaning and X is selected from the group comprising fluorine, chlorine and bromine, in the presence of powdered potassium hydroxide and at least one aprotic solvent selected from the group comprising dimethyl sulfoxide and dimethoxyethane at temperatures between 0 and 100° C, at least 1 mol of potassium hydroxide being used per mole of halogen compound.

5. The process as claimed in patent claim 4, wherein powdered potassium hydroxide is suspended in the aprotic solvent, the phosphine is added and the halogen compound is metered into this suspension in the course of 0.1 to 2 hours, and this reaction mixture is allowed to react for a further 4 to 12 hours at temperatures between 20 and 100° C.

6. The process as claimed in patent claim 4, wherein, to purify the tertiary phosphine, the reacted reaction mixture is stirred with water and the tertiary phosphine is extracted from it with methylene chloride, the extract is dried over solid potassium hydroxide, the extract is evaporated under a vacuum of 0.01 mbar and at a temperature of 20 to 100° C. and the oily residue is crystallized in ethanol.

* * * * *